United States Patent [19]

Ohno et al.

[11] Patent Number: 5,628,934
[45] Date of Patent: May 13, 1997

[54] PHOTOCHROMIC COLOR RENDERING REGULATORY COMPOSITION AND COSMETICS

[75] Inventors: Kazuhisa Ohno, Tokyo-to; Shigenori Kumagai, Machida; Fukuji Suzuki, Atugi; Nobuhisa Tsujita, Machida, all of Japan

[73] Assignee: Shiseido Co. Ltd., Tokyo, Japan

[21] Appl. No.: 351,050

[22] Filed: Nov. 28, 1994

Related U.S. Application Data

[63] Continuation of Ser. No. 979,234, Nov. 20, 1992, abandoned, which is a continuation-in-part of Ser. No. 455,320, Feb. 28, 1990, abandoned.

[30] Foreign Application Priority Data

Jun. 1, 1988 [JP] Japan .................. 63-132619

[51] Int. Cl.$^6$ .................. G02B 5/23; A61K 7/021
[52] U.S. Cl. .................. 252/586; 252/588; 424/63; 424/64; 424/69
[58] Field of Search .................. 252/586, 588; 424/63, 64, 69

[56] References Cited

U.S. PATENT DOCUMENTS

| | | | |
|---|---|---|---|
| 2,129,836 | 9/1938 | Goodman | 167/91 |
| 2,585,461 | 2/1952 | Hirsch | 23/148 |
| 3,579,356 | 5/1971 | Miller et al. | 99/148 |
| 3,592,940 | 7/1971 | Quesada | 99/148 |
| 5,486,354 | 1/1996 | DeFossez et al. | 424/63 |

FOREIGN PATENT DOCUMENTS

| | | |
|---|---|---|
| 0191292 | 8/1986 | European Pat. Off. . |
| 61-17422 | 1/1986 | Japan . |
| 61-118311 | 6/1986 | Japan . |
| 61-234921 | 10/1986 | Japan . |
| 62-34962 | 2/1987 | Japan . |
| 63-72620 | 4/1988 | Japan . |
| 63-135325 | 6/1988 | Japan . |
| 63-139120 | 6/1988 | Japan . |

OTHER PUBLICATIONS

Gomis, WPI Acc. No.: 89-287376/40—Abstract of ES 2005773.

Primary Examiner—Philip Tucker
Attorney, Agent, or Firm—Ronald R. Snider

[57] ABSTRACT

The present invention is a photochromic color rendering regulatory composition and cosmetics characterized in comprising of an inorgamic compound having photochromic property. Photochromic inorganic compounds colors the composition and cosmetics suitably according to the change in light intensity.

Therefore, composition and cosmetics of the present invention can regulate appropriate the tendency in which the color of objects looks whiter when the light intensity is strong and it looks blacker when it is weak, and can always provide constant color rendering.

23 Claims, 1 Drawing Sheet

PHOTOCHROMIC COLOR RENDERING REGULATORY COMPOSITION AND COSMETICS

This application is a continuation of application Ser. No. 07/979,234, filed Nov. 20, 1992, now abandoned, which is a continuation-in-part of now abandoned application Ser. No. 07/455,320, filed Feb. 28, 1990.

TECHNICAL FIELD

The present invention relates to a photochromic color rendering regulatory composition and cosmetics and in particular, to the improvement of such photochromic agent.

BACKGROUND ART

The property of changing color when one substance is irradiated with light and then returning to its original color when such irradiation is stopped is referred to as a photochromic or phototropic property. For example, this is used in light regulating glass, etc. which contains a photochromic substance.

In addition, in the field of cosmetics also, color variable make-up, which changes color using photochromic properties, is known (Japanese Laid-open Publication No. 56-49312 and No. 56-10079), and applications in an even broader range of fields are expected in the future.

However, conventional photochromic substances have been used only for the purpose of controlling the transmission of light or for the change in color tone itself. These have not been used for controlling changes in color rendering by reflected light.

Nothwithstanding, in the case of, for example, applying foundation to the face, even if the color of the made up skin is suitable when viewed indoors, the skin appears somewhat white when viewed under the rays of the sun. On the other hand, in the case of the color of made up skin is suitable under the rays of the sun, the skin appears somewhat dark when viewed indoors. In this manner, it has become clear that even in the case of using the same foundation product, depending on the intensity of the light, the resulting image subjectively changes considerably.

Further, in regard to the relationship between light intensity and color rendering properties, the inventors conducted the following experiment to further clarify this problem.

To begin with, foundation that is used normally, and foundation products having color values that are 0.2 and 0.5 lower in appearance were applied to the faces of female panelers having average skin color. The results were judged by 10 evaluators under both indoor and outdoor conditions. Evaluations were made using the 5 grades indicated below after which the average values of the 20 panel members were determined.

| Score | Color of Made Up Face |
|---|---|
| +2 | Dark and unnatural |
| +1 | Somewhat dark |
| 0 | Natural |
| −1 | Somewhat light |
| −2 | Light and unnatural |

The results of this experiment are indicated in Table 1.

TABLE 1

| | Type of Foundation | | |
|---|---|---|---|
| | Normal Product | Color Value −0.2 | Color Value −0.5 |
| Indoors: | | | |
| 200 Lux | 0 | +1.2 | +1.3 |
| 400 Lux | −1.1 | 0 | +1.1 |
| Outdoors: | | | |
| 10,000 Lux or greater | −1.3 | −1.2 | 0 |

As is clear from Table 1 above, foundation products having a lower color value appear more natural under outdoors rather than indoors. In addition, in bright locations, even when indoors, darker colored foundations appear more natural.

In this way, unless the color value is changed according to the intensity of the light, it is not possible to maintain natural color rendering with respect to what is subjectively considered to be natural.

However, most of the conventional variable color make-up cosmetics which contain photochromic compounds use spiropyrane-based compounds. And the enjoyment of the change in color could be obtained by the cosmetics, but these could not regulate the changes in color rendering of the cosmetics with respect to light intensity. As such, the problem of conventional cosmetics with which make up skin appears attractive indoors but appears excessively white under the rays of the sun still remains unsolved.

In addition, in the case of organic photochromic agents, the degree of color change does not shift gradually correspondingly to the change of light intensity, but rather, color change occurs rapidly at a certain fixed light intensity. This makes such organic photochromic agents unsuitable for regulating changes in color rendering accompanying changes in light intensity. Furthermore, in the case of use in cosmetics, etc., the safety of organic photochromic agents with respect to the human body is not sufficiently confirmed and moreover, various other issues remain unknown, such as the occurrence of photodegradation.

On the contrary, inorganic photochromic agents such as titanium oxide are thought to be unable to obtain a sufficient degree of coloring to be able to regulate color rendering at a fixed level even when blended into ingredients such as foundation due to the color change of the inorganic photochromic agent itself being comparatively small.

DISCLOSURE OF THE INVENTION

The present invention has been completed by considering the above-described problem of the prior art and an object of the present invention is to provide a photochromic color rendering regulatory composition and cosmetics which use such composition which is able to maintain color rendering at a constant level even in the presence of changes in light intensity.

As a result of intensive studies by the inventors in order to accomplish the objective of this inventions described above, differing from previous general knowledge, although photochromic inorganic compounds have a low degree of color change, it became clear that in the case of use as a pigment, it possesses superior coloring properties. And moreover, photochromic inorganic compound changes color itself in gradients corresponding to light intensity. This finding lead to the completion of this invention.

In other words, the photochromic color rendering regulatory composition of the present invention is characterized in containing from 1% to 60% by weight titanium oxide which possesses photochromic properties which composition is able to achieve color rendering constant with respect to the intensity of irradiated light.

The photochromic color rendering regulatory composition is characterized in that the photochromism of the composition is defined by;
$0.5 \leq A \leq 3$
$B \geq 70\%$
wherein A represents the color difference $\Delta E$ between (1) and (2), and B represents the color reversion ratio between (1) and (3). The measuring methods (1), (2), (3) are described below.

(1) A sample is produced by forming 5g of a powder in a medium-size square plate of 2.8×4.5 cm under a pressure of 30 Kg/cm². The sample which has been allowed to stand in a darkroom at room temperature for about 10 hours is measured by a colorimeter (Minolta CR-200). In the case of liquid composition, the liquid composition is spread on art paper with a thickness of 76 μm by an applicator. The art paper is dried and then used as the sample.

(2) One UV-A fluorescent lamp (FL20SBLB, produced by Toshiba Co., Ltd.) and one UV-B fluorescent lamp (FL20S-E, produced by Toshiba Co., Ltd.) are fixed at an interval of 15 cm, and using an ultraviolet light intensity measuring machine (SUV-T, produced by Toray Co., Ltd.), the height is adjusted so that the intensity of ultraviolet light is 2 mW/cm². The sample is placed at the height and irradiated with ultraviolet light by the above-descrived ultraviolet light intensity for 30 minutes, and the darkened color is measured in the same way as described in (1).

(3) After the darkened sample has been allowed to stand in the dark room for 3 hours, it is measured in the same way as described in (1).

The photochromic color rendering regulatory composition described in a further embodiment is characterized in that the photochromism of the titanium oxide is defined by;
$4 \leq A \leq 12$
$B \geq 70\%$
wherein A add B represent same as defined above.

The photochromic color .rendering regulatory composition described in another embodiment is characterized in that the photochromic titanium oxide in the composition is obtained by combining 95.0–99.95% by weight titanium oxide and 0.05–5.0% by weight of 1 or more types of iron powder or an iron compounds or mixture thereof followed by heating at 600°–1100° C.

The photochromic color rendering regulatory composition is characterized in containing photochromic titanium oxide from 1% by weight to 50% by weight.

The photochromic color rendering regulatory composition is characterized in containing of plate-form photochromic titanium oxide in the content from 10% by weight to 60% by weight.

The photochromic color rendering regulatory composition is characterized in that the surface of the photochromic inorganic compound is treated.

The photochromic color rendering regulatory composition is characterized in that a composite treatment is conducted on the surface of spherical powder by the photochromic inorganic compounds.

The photochromic color rendering regulatory cosmetic described is characterized in containing a photochromic color rendering regulatory composition according to the broadest embodiment in an amount such that the photochromic titanium oxide is present in an amount from 1% to 60% by weight based on the weight of the cosmetic composition.

The photochromic color rendering regulatory cosmetic is characterized in the photochromism of the composition is defined by:
$0.5 \leq A \leq 3$
$B \geq 70\%$
wherein A and B represent same as defined above.

The photochromic color rendering regulatory cosmetic is characterized in that the photochromism of the titanium oxide is defined by;
$4 \leq A \leq 12$
$B \geq 70\%$
wherein A and B represent same as defined above.

The photochromic color rendering regulatory cosmetic is characterized in that the inorganic compounds is one or more members selected from the group consisting of metal oxides, hydrates of the metal oxides, and consisting of two or more compounds from among the metal oxide and the hydrate.

The photochromic color rendering regulatory powdered cosmetic is characterized in that the photochromic titanium xide is used for the inorganic compound in the cosmetics, and is contained in an amount from 1% by weight to 30% by weight based on the weight of the cosmetic.

The photochromic color rendering regulatory powdered cosmetic is characterized in that the plate-form photochromic titanium oxide is used for the inorganic compound in the cosmetic, and is contained in an amount from 10% by weight to 60% by weight based on the weight of the cosmetic.

The photochromic color rendering regulatory liquid cosmetic described in another embodiment is characterized in containing titanium oxide for the inorganic compound in the cosmetics, and is contained in an amount from 1% by weight to 30% by weight based on the weight of the cosmetic.

The photochromic color rendering regulatory cosmetic is characterized in that the surface of the photochromic inorganic compound in the cosmetics is treated.

The photochromic color rendering regulatory cosmetic is characterized in a composite treatment is conducted on the surface of spherical powder by the photochromic inorganic compounds.

The following provides a detailed description of the content of the invention.

In this invention, examples of inorganic compounds which possess photochromic properties, or composition which contain said inorganic compound include metal oxides, hydrates of metal oxides, or composition consisting of two or more types of metal oxides and metal hydrates, zinc sulfide and $Hg_3S_2I_2$, etc.

Examples of metal oxides include titanium oxide, niobium oxide, silicon dioxide, aluminum oxide, zinc oxide, hafnium oxide, thorium oxide, tin oxide, thallium oxide, zirconium oxide, beryllium oxide, cobalt oxide, calcium oxide, magnesium oxide, molybdenum oxide, etc.

Examples of hydrates of metal oxides include titanium oxide hydrate, niobium oxide hydrate, silicon dioxide hydrate, aluminum hydroxide hydrate, zinc oxide hydrate, hafnium oxide hydrate, thorium oxide hydrate, tin oxide hydrate, thallium oxide hydrate, zirconium oxide hydrate, beryllium oxide hydrate, cobalt oxide hydrate, calcium oxide hydrate, magnesium oxide hydrate, molybdenum oxide hydrate, etc.

For cosmetic compositions, titanium oxide, aluminum oxide, zinc oxide, zirconium oxide, calcium oxide, magnesium oxide, or their hydrates, are preferred because these are chemically stable in terms of their being safe to the human body. From among these, titanium oxide as well as titanium oxide composites are the most preferred because of the large color change with respect to light of 310–420nm wavelength, and because of the rapid rate of return to the original color when irradiation of the above light is discontinued.

Examples of the titanium oxide used in this invention include titanium dioxide and low-oxide of titanium, etc. These may be mixtures or of the anatase type, rutile type or amorphous. And the shape of the particles of titanium oxide can be undefined shape, plate shape, and spherical shape. Average particle diameters on the order of 0.005–100 μm are typical. A titanium oxide blending amount of 95.0–99.95% by weight is favorable in the case of manufacturing of titanium oxide having photochromic properties.

In addition, in this invention, examples of the metals which are used to give photochromic properties to the titanium oxide include iron, chromium, copper, nickel and manganese, cobalt, molybdenum, etc., and their metal powders themselves, or their salts such as sulfates, chlorides, nitrates, acetates, etc., their oxides or their hydrates, etc.

Here, iron powder and iron compounds are favorable with respect to their being safe to the human body as well as in terms of providing photochromic properties.

In this invention, one or more of iron powder or iron compound or mixture thereof can be used. Examples of such iron compounds include iron salts such as iron sulfate, ferric chloride, iron nitrate and iron acetate, etc., iron oxides, and iron oxide hydrates, etc.

For giving the photochromic properties, a blending amount of 0.05–5.0% by weight is favorable, in the case of manufacturing the titanium oxide possessing photochromic properties. If the blending amount is too low, the expression of photochromic properties will be insufficient. When the blending amount is excessive, this is not desirable due to the occurrence of coloring produced by the metal.

In this invention, the titanium oxide which possesses photochromic properties that is manufactured from the titanium oxide and iron compounds described above, refers to that which demonstrates photochromic properties in the presence of light from the ultraviolet region to the infrared region. For example, in the case of use in cosmetics, in order to reduce the difference in the appearance of made up skin between that indoors and that outdoors, the compounds that possess photochromic properties with respect to ultraviolet light are preferred.

In addition, in this invention, it is also possible to use titanium oxide which possesses photochromic properties by compounding it with other inorganic or organic compounds. For example, titanium oxide possessing photochromic properties can be compounded with one or more of inorganic compounds such as mica, sericite, talc, kaolin, silica, barium sulfate, iron oxide, chromium oxide, copper oxide, nickel oxide, vanadium oxide, manganese oxide, cobalt oxide, calcium oxide, magnesium oxide, molybdenum oxide, zinc oxide, iron, chrome, copper, nickel, vanadium and manganese, etc., and organic compounds such as nylon, polymethyl methacrylate, polystyrene, epoxy resin and polyethylene, etc., by manipulations such as mixing, coating or sintering, etc.

Further, ordinary titanium oxide may also be compounded with other inorganic or organic compounds, and then it can be given photochromic properties.

Composites which contain titanium oxide possessing photochromic properties are obtained by, for example, the method indicated below. Following the addition of 0.05–5.0% by weight of an iron powder or iron compound to a titanium dioxide-coated complex such as titanium-mica or titanium-talc, etc., using a dry method such as a ball mill, or a wet method such as addition in the form of an aqueous solution, the titanium oxide complex is obtained by either heating at 600°–1100° C., or obtaining the complex allowing iron powder or iron compound to co-exist at the time of formation of a titanium dioxide complex by hydrolysis of titanyl sulfate, etc. followed by heating at 60020 –1100° C.

In this invention, the composite containing titanium oxide possessing photochromic properties may be further used following surface treatment using silicon, surface activator, surface alkoxylation, metal soap fatty acid, fluorocarbon resin, wax, etc. As a result of improving its dispersibility in this manner, the photochromic properties can be further improved.

The blended amount of titanium oxide possessing photochromic properties of this invention is 1.0–50.0% by weight, and preferably, 5.0–20.0% by weight, with respect to the total weight of the composition. When the blended amount is less than 1% by weight, the color changing function is unable to be sufficiently demonstrated. In addition, when the blended amount exceeds 50.0% by weight, the degree of color change becomes excessive.

In addition, in the case of manufacturing the titanium oxide possessing photochromic properties using plate-form titanium oxide, 10–60% by weight, and preferably, 10–40% by weight of the plate-form titanium oxide is blended with respect to the total weight of the composition. The reason for the blending amounts being larger in comparison to using ordinary titanium oxide for the raw material is that there is a decrease in specific surface area due to the larger particle diameter of plate-form titanium oxide and the degree of color change per unit weight is relatively less.

Similarly, when blending ordinary photochromic titanium oxide into powdered cosmetics like foundation and face powder, it is favorable to use 1–30% by weight. If less than 1% by weight is used, color rendering regulatory function will not be sufficiently demonstrated, and when in excess of 30% by weight, the change in color tone will be too wide making it impossible to maintain the color of made up skin constant and natural.

In the case of using plate-form titanium oxide for the photochromic titanium oxide, it is desirable to blend 10–60% by weight with respect to the powdered cosmetics.

In addition, when blending ordinary photochromic titanium oxide into liquid cosmetics such as suntan oil, etc., blending 1–30% by weight is desirable.

When the blending amount exceeds 30% by weight, the color becomes too white, so it is difficult to demonstrate its function as a liquid cosmetic product.

In addition to the titanium oxide possessing photochromic properties mentioned above, other ingredients which are used for the composition of ordinary cosmetics, etc. can be suitably blended into the composition of this invention as necessary. Examples of such ingredients that can be blended into the composition of this invention include inorganic powders such as talc, kaolin, mica, sericite, natural mica, phlogopite, synthetic mica, lepidolite, biotite, lithia mica, vermiculite, magnesium carbonate, calcium carbonate, diatomaceous earth, magnesium silicate, calcium silicate, aluminum silicate, barium silicate, barium sulfate, strontium silicate, metal tungstenate, silica, magnesium oxide, calcium oxide, zeolite, boron nitrate, and ceramic powder, etc.;

organic powders such as nylon powder, polyethylene powder, benzoguanamine powder, polytetrafluoroethylene powder and crystalline cellulose, etc.; inorganic white-type pigment such as titanium dioxide and zinc oxide, etc.; inorganic red-type pigment such as iron oxide (iron oxide red) and iron titanate, etc.; inorganic brown-type pigment such as gamma-iron oxide, etc.; inorganic yellow-type pigment such as yellow iron oxide and loess, etc.; inorganic black-type pigment such as black iron oxide and carbon black, etc.; inorganic purple-type pigment such as Mango Violet and cobalt violet, etc.; inorganic green-type pigment such as chromium oxide, chromium hydroxide and cobalt titanate, etc.; inorganic blue-type pigment such as ultramarine and prussian blue, etc.; pearl pigment such as titanium dioxide-coated mica, titanium dioxide-coated bismuth oxychloride, bismuth oxychloride, titanium oxide-coated talc, fish scale foil and blue titanium oxide-coated mica, etc.; metal powder pigment such as aluminum powder and copper powder, etc.; organic pigment such as red #201, red #202, red #204, red #205, red #220, red #226, red #228, red #405, orange #203, orange #204, yellow #205, yellow #401 and blue #404, etc.; organic pigment such as zirconium, barium or aluminum lake, red #3, red #104, red #106, red #227, red #230, red #401, red #505, orange #205, yellow #4, yellow #5, yellow #202, yellow #203, green #3 and blue #1, etc.; natural dye such as chlorophyll and β-carotene, etc.; various kinds of hydrocarbons such as squalane, liquid paraffin, vaseline, microcrystalline wax, ozocerite, ceresine, cetyl alcohol, hexadecyl alcohol, oleyl alcohol, cetyl-2-ethyl hexanoate, 2-ethylhexyl palmitate, 2-octyldodecyl myristate, 2-octylododecyl gum ester, neopentylglycol-2-ethyl hexanoate, isooctylate triglyceride, 2-octyldodecyl oleate, isopropyl myristate, isostearate triglyceride, coconut oil fatty acid triglyceride, olive oil, avocado oil, bees wax, myristyl myristate, mink oil, lanolin and dimethyl polysiloxane, etc.; fats, esters, higher alcohols, waxes, oils such as silicone oil, UV absorbers, antioxidant, preservatives, surface activate agents, humectant, perfume, water, alcohol and thickeners.

In the case of using the composition related to this invention, for example, cosmetics, the form of such cosmetics can be powder, cake, pencil, stick, ointment, liquid emulsion or cream.

Furthermore, by using plate-form titanium oxide possessing photochromic properties at this time, caking become difficult when removing the surface of the formed product with a puff. In addition, slippage when applying the cosmetics on the skin is improved thereby improving the usage qualities of the cosmetics.

As has been indicated above, in this invention, by blending titanium oxide possessing photochromic properties into compositions which are typically cosmetics, the composition having photochromic properties that could not be achieved by simply blending the conventional raw materials of cosmetics can be obtained.

For example, when titanium oxide possessing photochromic properties is applied to foundation, since the color of the foundation darkens under the rays of the sun, the difference between the color of made up skin indoors and the color of made up skin outdoors is decreased resulting in superior color rendering, thus making it possible to obtain a product which makes the skin appear attractive and natural under any type of light environment.

In addition, a major characteristic of this invention is that due to the high degree of effectiveness of UV blocking, the invention is able to prevent any detrimental effects on the skin due to excessive ultraviolet rays. On the other hand, since the invention has a high level of stability with respect to light, and since there is no occurrence of fatigue phenomena, it is thereby possible to obtain a stable product.

Further, titanium oxide possessing photochromic properties is much safer in comparison to organic substances possessing photochromic properties.

In addition to cosmetics, this invention can also be applied to paints and further to memory elements and sensor base materials which utilize photosensitivity.

BEST MODEL FOR CARRYING OUT THE INVENTION

Figure 1:
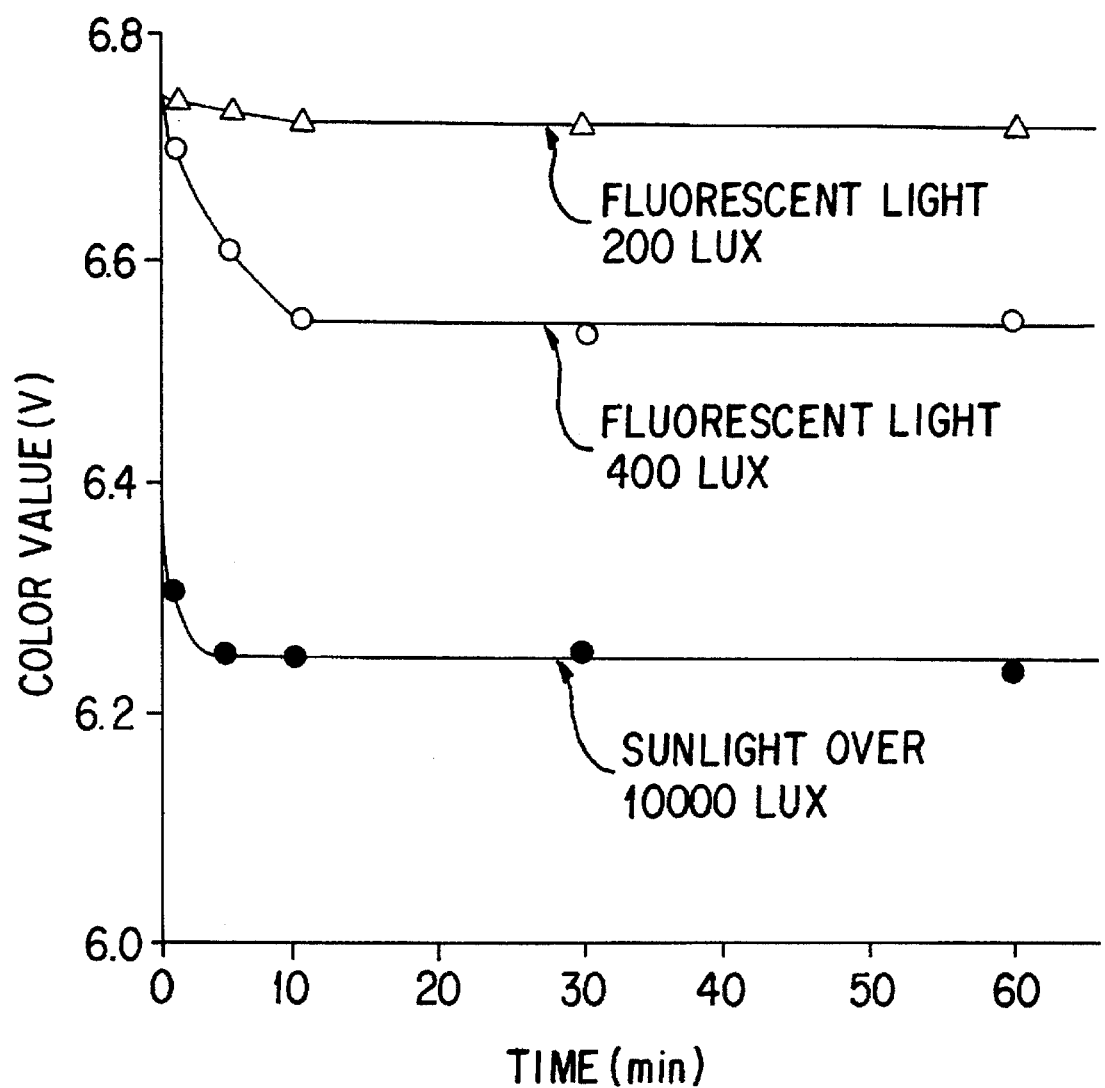
FIG. 1 is an explanatory diagram which indicates the relationship between the light intensity and the degree of color change of the photochromic titanium oxide related to this invention.

The following provides a detailed explanation of this invention using manufacturing examples and Examples. However, this invention is not limited to such examples and Examples. In addition, the blending amounts indicated in the following explanation are in the form of % by weight.

CHANGE OF FOUNDATION EXTERNAL COLOR BY PHOTOCHROMIC TITANIUM OXIDE

To begin with, a foundation having the following prescription was prepared and the change in the external color of the foundation caused by photochromic titanium oxide was examined.

| | |
|---|---|
| Photochromic Titanium Oxide | 20% |
| Talc | 10% |
| Mica | 55.7% |
| Iron Oxide | 2% |
| Squalane | 10% |
| Vaseline | 2% |
| Paraben | 0.2% |
| Perfume | 0.1% |
| | 100% |

The photochromic titanium oxide mentioned above that was prepared by adding 1 part iron hydroxide (FeOOH) to 99 parts titanium oxide followed by heating at 790° C. for 6 hours.

After the foundation which was formed as indicated above was molded into midplate, it was irradiated with sunlight for 10 minutes. The resulting color change was confirmed by colorimetry using a CMS-100S Colorimeter (Murakami Color Laboratories, Ltd. in Japan).

Those results are indicated in Table 2 below.

TABLE 2

| | | |
|---|---|---|
| Before Irradiation | H (Hue) | 2.9 YR |
| | V (Value) | 6.75 |
| | C (Chroma) | 4.5 |
| 10 Minutes of Sunlight | H (Hue) | 3.1 YR |
| | V (Value) | 6.25 |
| | C (Chroma) | 4.2 |

As is clear from Table 2, the color change of the foundation due to irradiation of light indicated a trend of decreased color value (V). When this trend is applied to Table 1 shown previously, this suggests that the change in color tone caused by light intensity is being regulated.

Further, FIG. 1 indicates the measurements of changes in color value (V) over time under sunlight and under fluorescent light.

In other words, it was discovered that the degrees of saturation of the respective changes in color value change according to the difference in light intensity between fluorescent light and sunlight, and that the degree of color change was greater under sunlight than under fluorescent light.

Moreover, color value decreases approximately 0.2 when irradiated with a 400 lux fluorescent lamp compared with irradiation with a 200 lux fluorescent lamp. In addition, color value decreases 0.5 during irradiation with sunlight at over 10,000 lux compared with irradiation with a 200 lux fluorescent lamp. Therefore, when this is applied to Table 1 indicated previously, it is understood that the natural color rendering is constantly being obtained.

In addition, in the case of compositions which are based on skin color such as foundation, changes in hue on the order of 0.2 and in chrome on the order of 0.3 are virtually no effect on color rendering.

Therefore, changes in color tone are expressed concentrating on color value making this invention particularly favorable in the case of desiring to maintain color rendering constant.

TINTING STRENGTH OF PHOTOCHROMIC TITANIUM OXIDE

As was stated previously, the degree of color change of photochromic titanium oxide is generally lower in comparison to organic photochromic agents. Therefore, it is considered to be quite natural that the tinting strength of photochromic titanium oxide is lower compared to that of organic photochromic agents.

Notwithstanding, the inventors were able to demonstrate the superior tinting strength of photochromic titanium oxide by performing the following experiment.

More specifically, the tinting strength of titanium oxide-based photochromic pigment was compared with that of spiropyrane-based photochromic pigment according to recipes A and B below.

| Recipe | A | B |
| --- | --- | --- |
| Ordinary Titanium Oxide | 15% | 20% |
| Photochromic Titanium Oxide | 5% | 0% |
| Spiropyrane | 0% | 5% |
| Talc | 5% | 0% |
| Mica | 58.9% | 59.0% |
| Iron Oxide | 3.0% | 2.9% |
| Squalane | 10% | 10% |
| Vaseline | 2% | 2% |
| Surface Activator | 1% | 1% |
| Perfume | 0.1% | 0.1% |
|  | 100 | 100 |

1,3,3-trimethylindolino-6'-nitrobenzo-pyrospiropyrane was used for the spiropyrane.

The foundations prepared according to the recipes above were molded into a midplate and the change in color value ΔV was measured before and after irradiation by sunlight for 10 minutes. Further, color difference was subjectively evaluated between a portion of the molded product that Was irradiated with sunlight for 10 minutes and a portion of a molded product that was not irradiated by covering one half of the surface of the molded product with aluminum foil.

Scoring was established as indicated below and the scores were determined to be the average values of the 20 panel members.

| Score | Color Change |
| --- | --- |
| 1 | No change |
| 2 | May have changed but hard to tell |
| 3 | Changed slightly |
| 4 | Changed |
| 5 | Changed considerably |

Those results are indicated in Table 3.

TABLE 3

|  | A | B |
| --- | --- | --- |
| ΔV | 0.15 | 0.02 |
| Subjective | 4.2 | 1.8 |

Based on the above results, contrary to previous general knowledge, although the color change of titanium oxide-based photochromic pigment itself is not considerable, it was made clear that in terms of tinting strength, it demonstrates values that are extremely larger in comparison to spiropyrane-based photochromic pigment.

STABILITY OF PHOTOCHROMIC TITANIUM OXIDE

The following examines the stability of photochromic titanium oxide.

Based on the results that have been stated previously, although it has been indicated that the tinting strength of photochromic titanium oxide is extremely superior, in the case of use in cosmetics or paints as a pigment, etc., if its stability under such conditions is low, there is essentially no significance to its regulating color rendering corresponding to changes in light intensity.

Therefore, the inventors conducted the following stability experiment.

Formed products made by the blending of the respective compounds A and B above were run through a xenon fade meter (Browning Fastness Tester FA-25XW, Toyo Rika Kogyo Ltd. in Japan) for 60 hours and allowed to stand in the dark for 24 hours were used for the samples. The difference in color value V was measured for each of the samples by comparing the color value V before and after irradiation for 10 minutes with sunlight.

Those results are indicated in Table 4.

TABLE 4

|  | A | B |
| --- | --- | --- |
| ΔV | 0.15 | 0 |

Based on the above results, it was understood that in contrast to the difference in color value of the titanium oxide-based color pigment remaining unchanged from that in Table 3 indicated previously, the photochromic properties of the spiropyrane-based photochromic pigment had nearly completely disappeared. Further, yellowing phenomena was also observed in the spiropyrane-based photochromic pigment due to photodegradation.

Therefore, titanium oxide-based photochromic pigment demonstrates an extremely high degree of stability in comparison to spiropyrane-based photochromic pigment, and is able to maintain superior color rendering regulatory function in the case of use in cosmetics and paints, etc. as pigment.

DEFINITION OF PHOTOCHROMISM

The favorable degree of photochromism was tested in the following manner in the present invention.

A sample was produced by forming 5 g of a powder in a medium-size square plate of 2.8×2.5 cm under a pressure of 30 Kg/cm$^2$.

As to the optical conditions, one UV-A fluorescent lamp (FL20SBLB, produced by Toshiba Co., Ltd.) and one UV-B fluorescent lamp (FL20S·E, produced by Toshiba Co., Ltd.) were fixed at an interval of 15 cm, and using an ultraviolet light intensity measuring machine (SUV-T, produced by Toray Co., Ltd.), the height was adjusted so that the intensity of ultraviolet light is 2 mW/cm$^2$.

The actual measurement was carried out in the following manner.

(1) The sample which has been allowed to stand in a darkroom at room temperature for about 10 hours is measured by a colormeter (Minolta CR-200).

(2) The sample was placed at the height and irradiated with ultraviolet light by the above-descrived ultraviolet light intensity for 30 minutes, and the darkened color was measured in the same way as described in (1).

(3) After the darkened sample was allowed to stand in the dark room for 3 hours, it was measured in the same way as described in (1).

As a result of the example described after, the photochromism of the composition is preferably;
$0.5 \leq A \leq 3$
$B \geq 70\%$
wherein A represents the color deference $\Delta E$ between (1) and (2), and B represents the color reversion ratio between (1) and (3).

If A is less than 0.5, the color rendering effect is not enough, and if A is larger than 3, the color changing degree become too strong.

Further, if the B is less than 70%, the color rendering effect can not be rapidly obtained when the light intensity is decreased.

Furthermore, the photochromism of the titanium oxide which possess photochromic properties is preferably;
$4 \leq A \leq 12$
$B \geq 70\%$ If A is less than 4, the color rendering effect of a composite which include the titanium oxide possessing the photochromic property is not enough, and if A is larger than 12, it becomes difficult to blend adequately titanium oxide possessing the photochromic property because of too strong photochromism.

CONTENT OF PHOTOCHROMIC TITANIUM OXIDE IN COMPOSITION

The following examines the blending amount of the titanium oxide-based photochromic pigment related to this invention.

Although photochromic titanium oxide causes a change in its color value according to light intensity, such change in color value must be to a degree such that color rendering is subjectively perceived to be constant.

If the content of photochromic titanium oxide is in excess and the color of the composition become too dark after exceeding the range of what appears attractive in response to an increase in light intensity, it is likely that a fixed color tone will not be able to be maintained.

On the contrary, if the content of photochromic titanium oxide is too low, it will be unable to adequately compensate for the tendency in which the color looks white accompanying increases in light intensity, thereby preventing it from maintaining color rendering at a fixed level.

Therefore, the content of photochromic titanium oxide contained in the composition is of important significance.

In response to this, the inventors conducted the following experiment.

First, the various blends of foundation indicated in Table 5 were prepared. The photochromic properties of these were then examined in the same manner as the previously described tinting strength test.

As a result, it was discovered that the favorable content of photochromic titanium oxide is 2% or more in blends when it contained in high covering power such as when total titanium oxide is roughly 20%, and the favorable content of photochromic titanium oxide is 1% or more in blends when it contained in low covering power such as when total titanium oxide is roughly 2%, and in such content, color tone is subjectively perceived to remain nearly constant even during changes in light intensity.

TABLE 5

|  | Total Titanium Oxide 20% | | | | | | Total Titanium Oxide 2% | | | |
| --- | --- | --- | --- | --- | --- | --- | --- | --- | --- | --- |
|  | C | D | E | F | G | H | I | J | K | L |
| Ordinary Titanium Oxide | 20 | 19 | 18 | 15 | 10 | 0 | 2 | 1.5 | 1 | 0 |
| Photochromic Titanium Oxide | 0 | 1 | 2 | 5 | 10 | 20 | 0 | 0.5 | 1 | 2 |
| Talc | 10 | 10 | 10 | 10 | 10 | 10 | 10 | 10 | 10 | 10 |
| Mica | 55.7 | 55.7 | 55.7 | 55.7 | 55.7 | 55.7 | 83.5 | 83.5 | 83.5 | 83.5 |
| Iron Oxide | 2 | 2 | 2 | 2 | 2 | 2 | 0.3 | 0.3 | 0.3 | 0.3 |
| Squalane | 10 | 10 | 10 | 10 | 10 | 10 | 4 | 4 | 4 | 4 |
| Vaseline | 2 | 2 | 2 | 2 | 2 | 2 | — | — | — | — |
| Paraben | 0.2 | 0.2 | 0.2 | 0.2 | 0.2 | 0.2 | 0.1 | 0.1 | 0.1 | 0.1 |
| Perfume | 0.1 | 0.1 | 0.1 | 0.1 | 0.1 | 0.1 | 0.1 | 0.1 | 0.1 | 0.1 |
| Total Results | 100 | 100 | 100 | 100 | 100 | 100 | 100 | 100 | 100 | 100 |

TABLE 5-continued

|  | Total Titanium Oxide 20% | | | | | | Total Titanium Oxide 2% | | | |
| --- | --- | --- | --- | --- | --- | --- | --- | --- | --- | --- |
|  | C | D | E | F | G | H | I | J | K | L |
| ΔV | 0 | 0.02 | 0.05 | 0.15 | 0.26 | 0.5 | 0 | 0.04 | 0.1 | 0.3 |
| Subjective Degree of Color Change | 0 | 1.5 | 3.2 | 4.2 | 5 | 5 | 1 | 1.9 | 3.6 | 5 |

On the other hand, although there are large changes in the maximum amount, according to the amount applied on skin or the color tone of the foundation, in general, a value of roughly 20% is favorable. When the amount of photochromic titanium oxide exceeds 30%, a tendency for it to demonstrate excessive changes in color was observed.

Further, in the case when the color of the value of the foundation itself is high, it is preferable to adjust the blended amount of photochromic titanium oxide to be slightly lower, and when this value is low, it is preferable to adjust the blended amount of photochromic titanium oxide to be slightly higher.

A detailed examination of the amount of photochromic titanium oxide blended into the composition was conducted based on Table 6.

To begin with, substances (1) through (8) were mixed in the blending amounts indicated in the row of Table 6. After adding and mixing in substances (9) through (13) to this mixture by heating and dissolving, the mixture was crushed with a pulverizer (Hosokawa Micron Ltd. in Japan). The mixture was then molded in the midplate to obtain the powder foundations.

Then, foundations M–T were applied to the faces of 10 Japanese women having average skin color. The color of the made up skin was then judged under indoor fluorescent light (200 lux) and outdoor sunlight using an evaluation procedure similar to that of Table 3. Those results are indicated in Table 6.

As is clear from this table, the scores of M, P, Q and T differed considerably between indoors and under sunlight. This can be understood to mean that a change in color rendering results according to the particular light intensity.

On the other hand, there was little difference in the scores of N, O, R and S whether indoors or under sunlight. This indicates that proper color rendering is being regulated irrespective of the light environment.

Therefore, with respect to photochromic titanium oxide A (manufacturing by Example 1, described after) which uses typical titanium oxide for its raw material, an amount on the order of 1–30% is suitable for blending into the foundation.

In addition, for photochromic titanium oxide D (manufactured by Example 4, described after) which uses plate-form titanium oxide for its raw material, it was clear that a blending amount of 10–60% is suitable.

TABLE 6

|  | M | N | O | P | Q | R | S | T |
| --- | --- | --- | --- | --- | --- | --- | --- | --- |
| (1) Photochromic Titanium Oxide A | 0.5 | 1 | 30 | 40 | — | — | — | — |
| (2) Photochromic Titanium Oxide D | — | — | — | — | 4 | 10 | 60 | 70 |
| (3) Talc | 10 | 10 | 10 | 10 | 10 | 10 | 10 | 10 |
| (4) Sericite | 68.67 | 67.88 | 37.3 | 26.6 | 65.19 | 58.88 | 7.3 | 4.6 |
| (5) Spherical Nylon Powder | 8 | 8 | 8 | 8 | 8 | 8 | 8 | 8 |
| (6) Red Iron Oxide | 0.1 | 0.2 | 0.7 | 0.9 | 0.1 | 0.2 | 0.7 | 0.9 |
| (7) Yellow Iron Oxide | 0.2 | 0.4 | 1.4 | 1.8 | 0.2 | 0.4 | 1.4 | 1.8 |
| (8) Black Iron Oxide | 0.01 | 0.02 | 0.1 | 0.2 | 0.01 | 0.02 | 0.1 | 0.2 |
| (9) Dimethyl Polysiloxane | 5.0 | 5.0 | 5.0 | 5.0 | 5.0 | 5.0 | 5.0 | 5.0 |
| (10) 2-ethylhexyl Palmitate | 5.0 | 5.0 | 5.0 | 5.0 | 5.0 | 5.0 | 5.0 | 5.0 |
| (11) Sorbitan Sesquioleate | 1.5 | 1.5 | 1.5 | 1.5 | 1.5 | 1.5 | 1.5 | 1.5 |
| (12) Preservative | 0.9 | 0.9 | 0.9 | 0.9 | 0.9 | 0.9 | 0.9 | 0.9 |
| (13) Perfume | 0.1 | 0.1 | 0.1 | 0.1 | 0.1 | 0.1 | 0.1 | 0.1 |
| Total Results | 100 | 100 | 100 | 100 | 100 | 100 | 100 | 100 |
| Indoors | 2.9 | 3.0 | 2.9 | 3.0 | 3.1 | 3.0 | 3.0 | 2.9 |
| Under Sunlight | 4.0 | 3.2 | 2.8 | 1.9 | 4.1 | 3.1 | 3.0 | 1.5 |

In addition to powdered composition such as those used in foundation, the following suntan oil was manufactured in order to examine the proper blended amount of photochromic titanium oxide in liquid composition.

|   | U | V | W | X |
|---|---|---|---|---|
| (1) Liquid Paraffin | 79.25 | 64.75 | 49.75 | 38.75 |
| (2) Silicon oil | 20.0 | 20.0 | 20.0 | 20.0 |
| (3) Vitamin E | 0.05 | 0.05 | 0.05 | 0.05 |
| (4) Perfume | 0.2 | 0.2 | 0.2 | 0.2 |
| (5) Photochromic Titanium Oxide D | 0.5 | 15.0 | 30.0 | 40.0 |
|   | 100 | 100 | 100 | 100 |

MANUFACTURING METHOD

After mixing ingredients (1) through (5) above, the suntan oil was obtained following degassing of the mixtures.

As a result of performing a practical usage test on the above compounds, V and W demonstrated suitable darkening under sunlight.

In contrast, the degree of darkening of U was insufficient and that of X was excessive.

Therefore, it was suggested that in the case of liquid cosmetics also, a blended amount of photochromic titanium oxide of roughly 1–30% was favorable.

The following provides detailed descriptions of embodiments of this invention together with an explanation of their photochromic properties.

PHOTOCHROMIC PROPERTIES TEST

Before presenting manufacturing examples of titanium oxide possessing photochromic properties, the following indicates the method of testing photochromic properties along with evaluation standards.

In other words, photochromic properties were investigated by irradiating with light having wavelengths of 200–700 nm for 5 seconds using a JASCO Monochrometer (Model CRM-FM).

The evaluation standards were as indicated below.
Darkness: ⊙ . . . Darkened extremely well
○ . . . Darkened well
□ . . . Darkened
Δ . . . Somewhat darkened
X . . . No darkening
Fading Time: The amount of time required for the darkened state to return to the original color when placed in a dark location.

MANUFACTURING OF PHOTOCHROMIC TITANIUM OXIDE

The following describes the methods used for manufacturing the photochromic titanium oxide used in this invention.

MANUFACTURING EXAMPLE 1

After mixing of 1 part iron hydroxide (FeOOH) having a particle diameter of 0.01 μm with 99 parts non-photochromic titanium dioxide having a particle diameter of 0.3 μm, which was commercially available and manufactured by the sulfuric acid methods, using a ball mixer; the mixture was heated for 180 minutes in air at 850° C. to obtain titanium oxide A possessing photochromic properties.

The photochromic degree A of this titanium oxide A was 7, and the reversion ratio B was 82%.

MANUFACTURING EXAMPLE 2

0.5 parts ferrous sulfate dissolved in 5.0 parts water was added and mixed into 99.5 parts commercially available non-photochromic titanium dioxide having a particle diameter of 0.03 μm, which was manufactured by chlorine methods, and then allowed to dry. This substance was heated for 1 hour in air at 850° C. to obtain the titanium oxide B possessing photochromic properties.

The photochromic degree A of this titanium oxide B was 11 and the reversion ratio B was 76%.

MANUFACTURING EXAMPLE 3

After adding 40 parts mica having an average particle diameter of 3 μm to 500 parts of a ½ M aqueous solution of titanyl sulfate, stirring at 80° C. and coating hydrous titanium dioxide onto the surface of the mica, the substance was filtered, washed and dried and 60 parts of titanium, dioxide-coated mica was obtained. 0.5 parts ferric chloride dissolved in 5 parts water of was then added and mixed into the above substance and then allowed to dry. This was then heated for 25 minutes in air at 950° C. to obtain 60 parts of a titanium oxide complex C possessing photochromic properties.

The photochromic degree A of this titanium oxide complex C was 5.2 and the reversion ratio B was 82%.

MANUFACTURING EXAMPLE 4

After uniform mixing using a henschel mixer of 0.05 parts ultra-fine iron powder having a particle diameter of 300 □ into 99.95 parts of thin plate titanium dioxide having a particle diameter of 5 μm, which was obtained by hydrolysis of titanium alkoxide followed by heating at 500° C., the compound was heated for 1 hour in air at 600° C. to obtain the thin plate titanium oxide D possessing photochromic properties.

The photochromic degree A of this titanium oxide D was 12 and the reversion ratio B was 74%.

EXAMPLE 1 FINE POWDER

| (1) Photochromic Titanium Oxide A | 5.2 |
|---|---|
| (2) Talc | 90.0 |
| (3) Iron Oxide | 2.5 |
| (4) Squalane | 2.0 |
| (5) Preservative | 0.2 |
| (6) Perfume | 0.1 |

MANUFACTURING METHOD (1)–(3) are mixed and a mixture of (4)–(6) which has been heated and dissolved was added to this followed by crushing. This was molded into a midplate to obtain the face powder.

The photochromic degree A of the Face Powder was 1.2 and the reversion ratio was 87%.

EXAMPLE 2 FACE POWDER

A face powder was manufactured by substituting titanium oxide A of Embodiment 1 with titanium oxide B which was obtained with Manufacturing Example 2.

The photochromic degree A of the Face Powder was 1.8 and the reversion ratio was 82%.

The products of the above example were examined in regard to wavelength of irradiated light and color change, as well as fading time.

Those results are indicated in Table 7 below.

TABLE 7

| Wavelength (nm) | Example 1 Darkening | Example 1 Fading Time | Example 2 Darkening | Example 2 Fading Time |
| --- | --- | --- | --- | --- |
| 200 | × | — | × | — |
| 300 | × | — | × | — |
| 310 | Δ | 15 sec. | × | — |
| 320 | Δ | 15 | × | — |
| 330 | □ | 100 | × | — |
| 340 | □ | 100 | × | — |
| 350 | ○ | 100 | × | — |
| 360 | ⊙ | 120 | × | — |
| 370 | ⊙ | 130 | Δ | 5 sec. |
| 380 | ⊙ | 120 | ○ | 5 |
| 390 | ○ | 100 | ⊙ | 10 |
| 400 | ○ | 100 | ⊙ | 10 |
| 410 | Δ | 15 | ○ | 5 |
| 420 | × | — | × | — |
| 430 | × | — | × | — |
| 500 | × | — | × | — |
| 600 | × | — | × | — |
| 700 | × | — | × | — |

As is clear from Table 7, the face powders of Embodiments 1 and 2 of this invention possess excellent photochromic properties.

In particular, darkening with wavelengths in the ultraviolet range is remarkable indicating that regulation of color rendering is favorable both indoors and outdoors.

EXAMPLE 3 POWDER FOUNDATION

| | |
| --- | --- |
| (1) Photochromic Titanium Oxide A | 20.0 |
| (2) Talc | 10.0 |
| (3) Sericite | 47.9 |
| (4) Spherical Nylon Powder | 8.0 |
| (5) Red Iron Oxide | 0.5 |
| (6) Yellow Iron Oxide | 1.0 |
| (7) Black Iron Oxide | 0.1 |
| (8) Polydimethyl Siloxane | 5.0 |
| (9) 2-ethylhexyl Palmitate | 1.5 |
| (10) Sorbitane Sesquioleate | 1.5 |
| (11) Preservative | 0.9 |
| (12) Perfume | 0.1 |

MANUFACTURING METHOD

After mixing of (1)–(9) with a henschel mixer and adding and mixing of (9)–(12) which had been heated and dissolved into the above mixture, the mixture was crushed with a pulverizer and molded into a midplate to obtain the powder foundation.

The photochromic degree A of the Powder Foundation was 2.6 and the reversion ratio B was 78%.

A powder foundation in which an equivalent amount of ordinary titanium dioxide was used in place of titanium oxide A possessing photochromic properties of ingredient (1) above was used for Comparative Example 1. In addition, a powder foundation in which an equivalent amount of polystylene powder containing 1,3,5-trimethyl-6'-nitrospiro (2'-H-1-benzopyrane-2,2'-indoline) was used in place of the titanium oxide A above was used for Comparative Example 2.

These powder foundations were prepared for comparison according to methods similar to those respective methods described above.

In comparison to the foundation of this invention, Comparative Examples 1 and 2 were applied, one product on each side, to the faces of 10 Japanese women having average skin color. The color of the made up skin both indoors under fluorescent light (200 lux) and outdoors under sunlight using the evaluation system indicated below was evaluated.

| Score | Color of Made Up Skin |
| --- | --- |
| 1 | Too dark |
| 2 | Dark |
| 3 | Natural |
| 4 | White |
| 5 | Too white |

The results were determined taking the average values of the 7 evaluators and are indicated in Table 8.

TABLE 8

| | Scores Indoors | Scores Under Sunlight |
| --- | --- | --- |
| Embodiment 3 | 3.00 | 3.13 |
| Comparative Example 1 | 3.14 | 4.85 |
| Comparative Example 2 | 3.00 | 3.93 |

The scores of the foundation of this invention remained essentially unchanged whether indoors or under sunlight. The made up skin appeared natural irrespective of the light environment.

On the other hand, although the color of skin on which the product of Comparative Example 1 was applied appeared natural indoors, the scores became larger when under sunlight with the product appeared considerably whiter.

Although the product of Comparative Example 2 did not demonstrate the whiteness of Comparative Example 1, the hue become somewhat yellowish making it unsuitable for the color of made up skin.

Next, sunlight was irradiated onto the formed surfaces of Embodiment 3, Comparative Example 1 and Comparative Example 2 for 30 seconds. The change in external color as well as the amount of time required for return to the original color were measured for each of these.

Those results are indicated in Table 9.

TABLE 9

| | Color Change | Fading Time |
| --- | --- | --- |
| Embodiment 3 | Darkening | 30 seconds |
| Comparative Example 1 | No Change | — |
| Comparative Example 2 | Browning | 2 minutes |

Based on the results indicated in Table 9, it was found that the powder foundation of this invention became darker in color and demonstrated a short fading time of 30 seconds.

Next, after irradiating the products which had been molded into midplate with a Xenon lamp for 200 hours, the color change for each of the products under sunlight was then confirmed. The testing method employed here is the same as that described previously.

Those results are indicated in Table 10.

TABLE 10

| | Color Change | Fading Time |
|---|---|---|
| Embodiment 3 | Darkening | 30 sec. |
| Comparative Example 1 | No change | — |
| Comparative Example 2 | No change | — |

Based on the results indicated in Table 10, although the powder foundation of this invention suffers no photodegradation, it can be seen that both Comparative Examples 1 and 2 are subject to such degradation.

As has been indicated above, the powder foundation of this invention demonstrates excellent color rendering of made up skin both indoors and under sunlight. It can also be understood that it demonstrates no photodegradation phenomena and is superior in comparison to the powder foundations of Comparative Examples 1 and 2.

EXAMPLE 4 DUAL-PURPOSE FOUNDATION

| | |
|---|---|
| (1) Compound Powder Possessing Photochromic Properties | 20.0% |
| (2) Silicone-treated Mica | 36.25% |
| (3) Silicone-treated Talc | 20.0% |
| (4) Silicone-treated Iron Oxide | 4.5% |
| (5) Silicone-treated Titanium Oxide | 6.5% |
| (6) Trimethyrol Propane Triisostearate | 5.0% |
| (7) Squalane | 3.0% |
| (8) Beeswax | 2.0% |
| (9) Sorbitan Trioleate | 1.0% |
| (10) Preservative | 0.5% |
| (11) Vitamin E | 0.05% |
| (12) Butylmethoxybenzoyl Methane | 1.0% |
| (13) Perfume | 0.2% |

MANUFACTURING METHOD

First of all, manufacturing of the compound powder possessing photochromic properties was performed as indicated below.

10 parts photochromic titanium oxide B was mixed with 90 parts spherical nylon powder (average particle diameter: 6 μm) with a henschel mixer. Next, the powder mixture that was obtained was mixed and compressed for 10 hours in a rotary ball mixer (Universal Ball Mixer, Yamato Kagaku, Ltd.) filled with alumina balls to obtain the compound powder.

In addition, the manufacturing of the foundation was performed as indicated below. Ingredients (1)–(5) were combined and ingredients (6)–(13) which had been heated and dissolved were added and mixed into this followed by crushing. The mixture was then molded into a midplate to obtain the dual-purpose foundation.

The photochromic degree A of the Dual-Purpose Foundation was 1.1 and the reversion ratio B was 82%.

The dual-purpose foundation related to this example exhibits superior color rendering both indoors and outdoors, and results in attractively made up skin, also demonstrates excellent ultra-violet screening, effects. Approximately twice the blended amount of photochromic titanium oxide was required in order to obtain similar effects without mixing photochromic titanium oxide B with the nylon powder.

The reason for this is that the composite powder possessing photochromic properties indicated above was homogeneously compounded on the surface of spherical nylon powder, and possessed improved dispersibility. It is thought that as a result of this, it is able to demonstrate superior regulation properties of color rendering.

EXAMPLE 5 SUNTAN OIL

| | |
|---|---|
| (1) Liquid Paraffin | 69.75 |
| (2) Silicone oil | 20.0 |
| (3) Vitamin E | 0.05 |
| (4) Perfume | 0.2 |
| (5) Titanium Oxide Complex C Possessing Photochromic Properties | 10.0 |

MANUFACTURING METHOD

After combining ingredients (1)–(4) and adding and dispersing ingredient (5). the mixture was degassed to obtain the suntan oil. The suntan oil darkened in color under sunlight and also demonstrated excellent effectiveness in screening out ultra-violet rays.

The photochromic degree A of the Suntan Oil was 0.7 and the color reversion ratio B was 88%.

EMBODIMENT 6 PAINT

| | a | b | c |
|---|---|---|---|
| (1) Photochromic Titanium Oxide A | 2 | 0 | 0 |
| (2) Photochromic Titanium Oxide D | 0 | 55 | 0 |
| (3) Hydrophobically-Treated Photochromic Titanium Oxide B | 0 | 0 | 10 |
| (4) Acryloid B-66 | 22 | 20 | 22 |
| (5) Xylene | 56 | 5 | 48 |
| (6) Mineral Spirit | 20 | 20 | 20 |
| | 100 | 100 | 100 |

MANUFACTURING METHOD

Ingredients (1)–(5) were kneaded together with a roll mill to obtain the acrylic paints a, b and c.

Paints a, b and c were each applied to a wall. When the brightness of the room was changed, the walls appeared lighter under darker light and had a somewhat darker, refined color tone under bright light.

Further, the photochromic titanium oxide of paint c demonstrated favorable dispersibility and demonstrated in particular superior color rendering regulatory effects and ultra-violet ray screening effects.

In addition, the hydrophobically-treated photochromic titanium oxide B was manufactured as indicated below.

After stirring 98 parts by weight photochromic titanium oxide B, 2 parts by weight methyl hydrogen polysiloxane equivalent to 65 parts SiH and 200 parts by weight dichloromethane for 10 minutes at 50° C., the dichloromethane was removed and the resulting material was subjected to a heating treatment for 3 hours at 190° C. to obtain the hydrophobically- treated photochromic titanium oxide B.

EXAMPLE 7 EMULSIFIED FOUNDATION

| | | |
|---|---|---|
| (1) | Zinc Oxide - Zirconium Oxide Composite Possessing Photochromic Properties | 1.0% |
| (2) | Stearic Acid | 1.5% |
| (3) | Isostearic Acid | 0.3% |
| (4) | Isopropyl Myristate | 4.0% |
| (5) | Squalane | 12.0% |
| (6) | POE Stearyl Ether | 1.5% |
| (7) | Glyceryl Monooleate | 0.5% |
| (8) | Cetyl Alcohol | 0.5% |
| (9) | Talc | 10.0% |
| (10) | Iron Oxide | 0.5% |
| (11) | Preservative | 0.15% |
| (12) | Triethanol Amine | 0.8% |
| (13) | Propylene Glycol | 6.0% |
| (14) | Montmorillonite | 0.5% |
| (15) | Purified Water | 60.55% |
| (16) | Perfume | 0.2% |

MANUFACTURING METHOD

After combining ingredients (12)–(15) and heating, followed by mixing in ingredients (1), (9) and (10) and crushing, the ingredients were dispersed in the mixture. Further, after gradual addition of the oil parts of ingredients (2)–(8), (11) and (16) which had been heated at 70° C. and dissolved into a mixture in advance, the resulting mixture was dispersed into an emulsion. This was then allowed to cool to room temperature to obtain the emulsified foundation.

When the foundation of this example was applied to the face and exposed to sunlight, the color value of the made up face decreased yielding an attractive made up face that appeared natural both indoors and outdoors.

EXAMPLE 8 NAIL ENAMEL

| | | |
|---|---|---|
| (1) | Alkyd Resin | 10.0% |
| (2) | Cotton Nitride | 13.0% |
| (3) | Acetyltributyl Citrate | 5.0% |
| (4) | Organic Denatured Montmorillonite | 1.0% |
| (5) | Toluene | 21.0% |
| (6) | Butyl Acetate | 37.7% |
| (7) | Ethyl Acetate | 5.3% |
| (8) | n-Butanol | 2.0% |
| (9) | Iron Oxide | 1.0% |
| (10) | Lithorulubin BCA | 0.3% |
| (11) | Phototropic Zinc Sulfide | 3.7% |

MANUFACTURING METHOD

Ingredients (5)–(8) were combined followed by addition of ingredients (1)–(9) followed by stirring and dissolving. Following this, ingredient (4) and ingredients (9)–(11) were added and dispersed.

The nail enamel obtained in this manner changes color under sunlight and together with maintaining constant color rendering, demonstrates excellent resistance to fatigue.

As has been described above, according to the compositions related to this invention, since such compositions have been made to contain photochromic titanium oxide, in addition to excellent stability, it is possible to obtain compositions having color tone that always subjectively appears constant unrelated to light intensity.

In addition, by using the cosmetics of this invention, it is possible to always make such made up skin appear attractive and natural irrespective of the particular light environment.

What is claimed is:

1. A photochromic color rendering regulatory cosmetic foundation consisting essentially of:

a cosmetic; and a photochromic color rendering composition in said cosmetic, said color rendering composition containing from 1% to 60% by weight titanium oxide which possesses photochromic properties which composition is able to achieve color rendering constant with respect to the intensity of irradiated light.

2. A photochromic color rendering regulatory cosmetic foundation according to claim 1, wherein the photochromism of the foundation is defined by;

$0.5 \leq A \leq 3$ $B \geq 70\%$, wherein A represents the color difference $\Delta E$ between (1) and (2), B represents the color reversion ratio between (1) and (3), and wherein (1), (2), and (3) are defined as follows:

(1) a sample is produced by forming 5 g of a powder in a medium-size square plate of 2.8×4.5 cm under a pressure of 30 Kg/cm$^2$ where the sample has been allowed to stand in a darkroom at room temperature for about 10 hours, is measured by a colorimeter;

(2) one UV-A fluorescent lamp and one UV-B fluorescent lamp are fixed at an interval of 15 cm, and using an ultraviolet light intensity measuring machine the height of which is adjusted so that the intensity of ultraviolet light is 2 mW/cm$^2$ the sample is placed at said adjusted height and irradiated with ultraviolet light by the above-described ultraviolet light intensity for 30 minutes, and the darkened color is measured in the same way as described in (1); and (3) after the darkened sample is allowed to stand in a dark room for 3 hours, it is measured in the same way as described in (1).

3. A photochromic color rendering regulatory cosmetic foundation according to claim 1, wherein the photochromism of the foundation is defined by;

$4 \leq A \leq 12$ $B \geq 70\%$, wherein A represents the color difference $\Delta E$ between (1) and (2), B represents the color reversion ratio between (1) and (3), and wherein (1), (2), and (3) are defined as follows:

(1) a sample is produced by forming 5 g of a powder in a medium-size square plate of 2.8×4.5 cm under a pressure of 30 Kg/cm$^2$ where the sample has been allowed to stand in a darkroom at room temperature for about 10 hours, is measured by a colorimeter;

(2) one UV-A fluorescent lamp and one UV-B fluorescent lamp are fixed at an interval of 15 cm, and using an ultraviolet light intensity measuring machine the height of which is adjusted so that the intensity of ultraviolet light is 2 mW/cm$^2$ the sample is placed at said adjusted height and irradiated with ultraviolet light by the above-described ultraviolet light intensity for 30 minutes, and the darkened color is measured in the same way as described in (1); and (3) after the darkened sample is allowed to stand in a dark room for 3 hours, it is measured in the same way as described in (1).

4. A photochromic color rendering regulatory cosmetic foundation according to claim 3, wherein the photochromic titanium oxide in the foundation is obtained by combining 95.0–99.95% by weight titanium oxide and 0.05–5.0% by weight of one or more types of iron powder or an iron compounds or mixture thereof followed by heating at 600°–1100° C.

5. A photochromic color rendering regulatory cosmetic foundation according to claim 3, containing photochromic titanium oxide in the content from 1–50% by weight.

6. A photochromic color rendering regulatory cosmetic foundation according to claim 3, containing of plate-form photochromic titanium oxide in the content from 10–60% by weight.

7. A photochromic color rendering regulatory cosmetic foundation according to claim 6, wherein a surface of the photochromic color rendering composition is treated with a material selected from the group consisting of silicon, surface activator, surface alkoxylation, metal soap, fatty acid, fluorocarbon resin and wax.

8. A photochromic color rendering regulatory cosmetic foundation according to claim 7, wherein treatment is on spherical powder surfaces of the photochromic inorganic compounds.

9. A photochromic color rendering regulatory cosmetic foundation consisting essentially of
a cosmetic; and
a photochromic color rendering regulatory composition in an amount such that photochromic titanium oxide is present in an amount from 1–60% by weight based on the weight of the cosmetic foundation which composition is able to achieve color rendering constant with respect to the intensity of irradiated light.

10. A photochromic color rendering regulatory cosmetic foundation containing a photochromic color rendering regulatory composition according to claim 1, wherein said cosmetic foundation is a nail enamel.

11. A photochromic color rendering regulatory cosmetic foundation according to claim 9, further including inorganic compounds which are one or more members selected from the group consisting of metal oxides, hydrates of the metal oxides, and comprising two or more compounds from among the metal oxide and the hydrate.

12. A photochromic color rendering regulatory cosmetic foundation according to claim 1, wherein said color rendering regulatory cosmetic foundation is blended into said cosmetic when said cosmetic is blended.

13. A photochromic color rendering regulatory cosmetic foundation according to claim 11, wherein the photochromic titanium oxide is used for the inorganic compound in the cosmetic foundation, and is contained in an amount from 1–30% by weight based on the weight of the cosmetic foundation.

14. A photochromic color rendering regulatory cosmetic foundation according to claim 9, wherein plate-form photochromic titanium oxide is used for the inorganic compound in the cosmetic foundation, and is contained in an amount from 10–60% by weight based on the weight of the cosmetic foundation.

15. A photochromic color rendering regulatory cosmetic foundation according to claim 9, containing titanium oxide inorganic compound in the cosmetics and which is contained in an amount from 1–30% by weight based on the weight of the cosmetic foundation.

16. A photochromic color rendering regulatory cosmetic foundation according to claim 9, wherein a surface of the photochromic color rendering composition is treated with a material selected from the group consisting of silicon, surface activator, surface alkoxylation, metal soap, fatty acid, fluorocarbon resin and wax.

17. A photochromic color rendering regulatory cosmetic foundation according to claim 9, wherein a composite treatment by the photochromic color rendering regulatory composition is conducted on a surface of a spherical powder.

18. A photochromic color rendering regulatory cosmetic foundation consisting essentially of:
a cosmetic, and
a photochromic color rendering composition containing from 1% to 60% by weight titanium oxide which possesses photochromic properties,
wherein said cosmetic foundation is able to achieve color rendering constant as perceived by the human eye.

19. A photochromic color rendering regulatory cosmetic foundation according to claim 1, wherein the photochromism of the photochromic color rendering composition is defined by;
$0.5 \leq A \leq 3$
$B \geq 70\%$,
wherein A represents the color deference $\Delta E$ between (1) and (2),
B represents the color reversion ratio between (1) and (3), and
wherein (1), (2), and (3) are defined as follows:
(1) a sample is produced by forming 5 g of a powder in a medium-size square plate of 2.8×4.5 cm under a pressure of 30 Kg/cm$^2$ where the sample has been allowed to stand in a darkroom at room temperature for about 10 hours, is measured by a colorimeter;
(2) one UV-A fluorescent lamp and one UV-B fluorescent lamp are fixed at an interval of 15 cm, and using an ultraviolet light intensity measuring machine the height of which is adjusted so that the intensity of ultraviolet light is 2 Mw/cm$_2$, the sample is placed at said adjusted height and irradiated with ultraviolet light by the above-described ultraviolet light intensity for 30 minutes, and the darkened color is measured in the same way as described in (1); and
(3) after the darkened sample is allowed to stand in a dark room for 3 hours, it is measured in the same way as described in (1).

20. A photochromic color rendering regulatory cosmetic foundation according to claim 1, wherein the photochromism of the foundation is defined by
$0.5 \leq A \leq 3$, and
$B \geq 70\%$,
wherein A represents the color difference $\Delta E$ between (1) and (2),
B represents the color reversion ratio between (1) and (3), and
wherein (1), (2), and (3) are defined as follows:
(1) a 5 g powder sample is formed in a plate of 2.8×4.5 cm under a pressure of 30 kg/cm$^2$, allowed to stand in a dark room at room temperature for about 10 hours, and measured by a colorimeter;
(2) said sample is irradiated for 30 minutes with 2 mW/cm$^2$ ultraviolet light from one each UV-A and UV-B fluorescent lamp spaced 15 cm therebetween, and measured by a colorimeter; and
(3) said sample is allowed to stand in a dark room for 3 hours, and measured by a colorimeter.

21. A photochromic color rendering regulatory cosmetic foundation according to claim 1, wherein the photochromism of the foundation is defined by;
$0.5 \leq A \leq 3$
wherein A represents the color deference $\Delta E$ between (1) and (2), wherein (1), and (2) are defined as follows:

(1) a sample is produced by forming 5 g of a powder in a medium-size square plate of 2.8×4.5 cm under a pressure of 30 Kg/cm² where the sample has been allowed to stand in a darkroom at room temperature for about 10 hours, is measured by a colorimeter; and (2) one UV-A fluorescent lamp and one UV-B fluorescent lamp are fixed at an interval of 15 cm, and using an ultraviolet light intensity measuring machine the height of which is adjusted so that the intensity of ultraviolet light is 2 Mw/cm² and the sample is placed at said adjusted height and irradiated with ultraviolet light by the above-described ultraviolet light intensity for 30 minutes, and the darkened color is measured in the same way as described in (1).

22. A photochromic color rendering regulatory cosmetic foundation according to claim 1, wherein the photochromism of the photochromic color rendering composition is defined by;

$0.5 \leq A \leq 3$ wherein A represents the color difference ΔE between (1) and (2), wherein (1) and (2) are defined as follows:

(1) a sample is produced by forming 5 g of a powder in a medium-size square plate of 2.8×4.5 cm under a pressure of 30 Kg/cm² where the sample has been allowed to stand in a darkroom at room temperature for about 10 hours, is measured by a colorimeter; and (2) one UV-A fluorescent lamp and one UV-B fluorescent lamp are fixed at an interval of 15 cm, and using an ultraviolet light intensity measuring machine the height of which is adjusted so that the intensity of ultraviolet light is 2 Mw/cm² and the sample is placed at said adjusted height and irradiated with ultraviolet light by the above-described ultraviolet light intensity for 30 minutes, and the darkened color is measured in the same way as described in (1).

23. A photochromic color rendering regulatory cosmetic foundation according to claim 1, wherein the photochromism of the foundation is defined by $0.5 \leq A \leq 3$, wherein A represents the color difference ΔE between (1) and (2), wherein (1) and (2) are defined as follows:

(1) a 5 g powder sample is formed in a plate of 2.8×4.5 cm under a pressure of 30 kg/cm², allowed to stand in a dark room at room temperature for about 10 hours, and measured by a colorimeter; and (2) said sample is irradiated for 30 minutes with 2 mW/cm² ultraviolet light from one each UV-A and UV-B fluorescent lamp spaced 15 cm therebetween, and measured by a colorimeter.

* * * * *